United States Patent
Lee et al.

(10) Patent No.: US 6,908,625 B2
(45) Date of Patent: Jun. 21, 2005

(54) COSMETIC MATERIAL CONTAINING TRIPLE- ENCAPSULATED RETINOL

(75) Inventors: Seung Ji Lee, Chungcheongnam-do (KR); Byoung Kee Jo, Kyungki-do (KR); Young Jin Lee, Chungcheongnam-do (KR); Chun Mong Lee, Chungcheongnam-do (KR)

(73) Assignee: Coreana Cosmetics Co., Ltd. (KR)

( * ) Notice: Subject to any disclaimer, the term of this patent is extended or adjusted under 35 U.S.C. 154(b) by 247 days.

(21) Appl. No.: 10/011,081

(22) Filed: Dec. 7, 2001

(65) Prior Publication Data

US 2003/0118616 A1 Jun. 26, 2003

(30) Foreign Application Priority Data

Sep. 7, 2001 (KR) ......................... 2001-55103

(51) Int. Cl.⁷ ............................ A61K 9/127; A61K 7/00
(52) U.S. Cl. ........................ 424/450; 424/401; 514/725; 514/887; 514/937
(58) Field of Search ................................ 424/450, 401; 514/725, 887, 937–943

(56) References Cited

U.S. PATENT DOCUMENTS

| | | | |
|---|---|---|---|
| 3,906,108 A | 9/1975 | Felty | |
| 4,247,547 A | 1/1981 | Marks | |
| 4,603,146 A | 7/1986 | Kligman | |
| 4,720,353 A | 1/1988 | Bell | |
| 4,826,828 A | 5/1989 | Wilmott et al. | |
| 4,877,805 A | 10/1989 | Kligman | |
| 5,256,422 A | * 10/1993 | Albert et al. | ............... 424/450 |
| 5,693,330 A | 12/1997 | Granger | |
| 5,858,398 A | * 1/1999 | Cho | ............... 424/450 |
| 5,885,595 A | 3/1999 | Corey | |
| 6,296,870 B1 | * 10/2001 | Needham et al. | ........... 424/450 |
| 6,464,966 B1 | * 10/2002 | Simon | ............... 424/70.12 |

FOREIGN PATENT DOCUMENTS

| | | | |
|---|---|---|---|
| EP | 0 140 085 | * | 5/1985 |
| EP | 0440398 B1 | | 12/1993 |

* cited by examiner

*Primary Examiner*—Gollamudi S. Kishore
(74) *Attorney, Agent, or Firm*—Akerman Senterfitt

(57) ABSTRACT

The present invention concerns stabilized cosmetic material containing triple-encapsulated retinol. Unstable, fat-soluble retinol is stabilized firstly by addition into vesicles consisting of nonionic surface-active agent, cholesterol and cholesteryl ester. The firstly stabilized retinol(vesicle) is subsequently inserted into sphingosomes (a kind of multi lamellar liposome) consisting of lecithin and ceramide. Finally the double-encapsulated retinol (sphingosome) is inserted into lamellar liquid-crystal emulsifying base, thereby being triply encapsulated.

16 Claims, No Drawings

COSMETIC MATERIAL CONTAINING TRIPLE- ENCAPSULATED RETINOL

FIELD OF THE INVENTION

The present invention concerns stabilized cosmetic material containing triple encapsulated retinol. In concrete terms, unstable and fat-soluble retinol is stabilized firstly by addition into vesicles consisting of nonionic surface-active agent, cholesterol and cholesteryl ester. The firstly stabilized retinol(vesicle) is subsequently inserted into sphingosomes (a kind of multi lamellar liposome) consisting of lecithin and ceramide. Finally the double encapsulated retinol (sphingosome) is added into a lamellar liquid-crystal emulsifying base. Thusly, useful cosmetic material, which diminishes wrinkling, skin irritation and improves moisturizing effect, is obtained.

BACKGROUND OF THE INVENTION

Chronoaging results in general degradation of the skin. Wrinkling and thickening of the skin induced by solar light result in sagging, reduced elasticity of skin, dry skin and mottling, and other harmful effects are additively increased by exposure to sunlight and this phenomenon is called "photoaging". Deterioration of the epidermis and dermis, wrinkling, yellowing, thickening and reduced elasticity of skin are all associated with photoaging.

To solve this problem, uses of retinoid (vitamin A) have been reported in U.S. Pat. Nos. 4,603,146 and 4,877,805. There are Retinol (Vitamin A alcohol), Retinal (Vitamin A aldehyde), Retinyl acetate, Retinyl propionate, Retinyl linoleate and Retinyl palmitate in the Retinoid group. Among elements of retinoid group, retinol is a compound which can be naturally found in the human body and is essential in the specialization and growth of epithelium. Moreover, retinol is superior to other retinoids (such as retinoic acid) in terms of safety for living creatures, so retinol is suitable for skin-care cosmetic material. In case of excessive intake, retinol is chiefly stored as an inactive form of retinyl palmitate, and a small quantity is stored as an inactive form of retinyl acetate in the human body.

Skin care compositions containing retinoids have become quite prominent in recent years and particularly retinol, also known as Vitamin A, is well known as a treatment for acne, so many medical or pharmaceutical goods containing retinol, including types of ointments are produced and consumed. Even more recently, many other benefits of retinol have been revealed, and the typical examples are effects against photoaging and sun-damage.

In spite of these beneficial effects, retinal is easily oxidized and denatured, and loses its characteristic color, odor when contacting with air, oxygen, heat or aqueous solution, so original potency is lowered significantly. Also, pure retinal induces skin irritation even when used in small amounts. Due to these drawbacks, retinal has been limitedly incorporated into cosmetic formulations.

Many studies have been conducted to stabilize retinal in a cosmetic composition. U.S. Pat. No. 08-769130 reports a double-encapsulation method which comprises the steps of (a)first-encapsulating the retinal with filming materials such as glycosaminoglycan to give a microcapsule; and (b) encapsulating the microcapsule of the step (a) with gellan gums. This technique stabilizes doubly retinal, however the second-encapsulating with gellan gums is a kind of an open matrix system, therefore this method is limitedly effective in protecting retinal from oxygen, air or heat.

There has also been proposed an oil-in-water type (O/W type) emulsion wherein retinoic acid is stabilized with a fat-soluble antioxidant such as BHT (butylated hydroxytoluene) and dl-a-tocopherol or a chelating agent such as EDTA in U.S. Pat. No. 3,906,108. U.S. Pat. No. 4,247,547 reports an oil-in-water type (O/W type) emulsion wherein fat-soluble active material is stabilized with a fat-soluble antioxidant consisting of tocopherol, citric acid.

U.S. Pat. No. 4,826,828 reports a water-in-oil type (W/O type) emulsion wherein retinol, retinyl acetate and retinyl palmitate are stabilized by an antioxidant such as BHT (butylated hydroxytoluene), or BHA (butylated hydroxyanisole). U.S. Pat. No. 4,720,353 reports a water-in-oil type (W/O type) emulsion wherein retinol is stabilized with an antioxidant such as BHA (butylated hydroxyanisole), ascorbic acid or tocopherol.

E.P. 0440398 (B1) reports an oil-in-water type (O/W type) emulsion wherein retinol is stabilized with one or more kinds of water-soluble antioxidants or chelating agents to improve chemical stability of retinol. A European Patent application also reports an oil-in-water type (O/W type) emulsion wherein retinol is stabilized with a chelating agent, water, fat-soluble antioxidants and free-base type imidazole.

As stated above, most patents refer to stabilizing methods wherein antioxidants and chelating agents are the prime elements. However the only difference between patent techniques is the kind of chelating agents and properties of antioxidants used, so with these methods, retinol cannot be protected from oxygen, moisture or heat effectively.

SUMMARY OF THE INVENTION

To solve the problems stated above, the inventor of this invention stabilized unstable fat-soluble cosmetically active material with the method comprising the steps of (a) stabilizing retinol with nonionic surface-active agent vesicles consisting of nonionic surface-active agent, cholesterol, phytosterol and oily carrier; (b) stabilizing first-stabilized retinol with sphingosome consisting of lecithin, ceramide and oily carrier; (c) stabilizing double-stabilized retinol three times by adding it into an O/W type lamellar liquid-crystal structure consisting of a nonionic surface-active agent, higher fatty acid, ceramide, cholesterol and phytosterol. By this kind of multilayer trapping, retinol can be stabilized effectively against air, water, and heat.

With the present triple covering, the functional lifetime of retinol is maintained for a long time, so affinity to the skin is improved and skin irritation is minimized.

In short, first, there are provided triple layers that have retinol confined within the primary layer so as to bring the retinol into contact with air and water as little as possible. Second, because of the triple layers consisting of lecithin, ceramide and cholesterol, which have excellent affinity for the skin, permeability and affinity to the skin of produced cosmetic materials are improved. Third, in application to the skin, triple stabilized retinol is released to the skin very slowly, so skin irritation can be minimized remarkably.

DETAILED DESCRIPTION OF THE INVENTION

The present invention concerns stabilized cosmetic material containing triple-encapsulated retinol. In concrete terms, retinol is stabilized firstly by addition into vesicles. The first stabilized retinol is subsequently inserted into sphingosomes. Finally the double encapsulated retinol is added into an oil-in water (O/W) type lamellar liquid-crystal structure and stabilized three times. Because retinol can be protected from oxygen, moisture and heat almost perfectly, it is released to the skin very slowly and skin-irritation is minimized.

The present invention will be described in more detail as follows.

Stabilization Method I:

Retinol is added into a nonionic surface-active agent vesicles and firstly stabilized.

The above nonionic surface-active agent vesicle is a monolayered microspore, which consists of a nonionic surface-active agent, cholesterol, phytosterol and oily carrier and formed by passage through a high-pressure (500~1500 bar) emulsifier. Retinal is contained in the core space of the vesicle which has a mean diameter of 10~50 nanometres The detailed composition of the vesicles comprises: nonionic surface-active agent in an amount of 0.01–10.0 weight %, alkylphosphate in an amount of 0.1~10.0 weight %, fat-soluble active material in an amount of 0.1~20.0 weight %, oily carrier in an amount of 5.0~30.0 weight % cholesterol and its derivative, phytosterol and its derivatives in an amount of 1.0~20.0 weight %, polyhydric alcohol aqueous solution in an amount of 20.0~55.0 weight % (polyhydric alcohol 1.0~20.0 weight %) with respect to the entire vesicle composition.

The nonionic surface-active agent can be selected from among the group consisting of polyoxyethylene alkyl ether, polyoxyethylene cholesteryl ester, polyoxyethylene sorbitan ester, polyglyceryl alkyl ester, polyoxyethylene alkyl ester, sucrose ester and so on. Alkylphosphate should be selected from among mono, di, tri-alkyl phosphate, polyoxyethylene alkyl phosphate and so on. In this invention, oily carrier is a common name for most oily material, which is in liquid state at room temperature, and can be selected from among vegetable oil, animal oil, synthetic oil, mineral oil, silicone oil, silicone derivatives and so on. Cholesterol and its derivatives can be selected from cholesteryl alkylate and cholesteryl sulfate produced by esterification of fatty acid, and natural or synthetic cholesterol. Phytosterol and its derivative can be selected from among beta-sitosterol, beta-sitosterol sulfate and so on. Polyhydric alcohol can be selected from among glycerine, propylene glycol, dipropylene glycol, butylene glycol, isopropylene glycol, pentylene glycol and so on.

Stabilization Method II:

The water-phase composition, which consists of phospholipid, ceramide, oily carrier, polyol and ethanol, is mixed uniformly and passed through a high-pressure (500~1500 bar) emulsifier. Then firstly-stabilized retinol (vesicle) is added, then the mixture must be passed through a high-pressure (500~1500 bar) emulsifier again. Thereby, the vesicles are encapsulated and second-stabilized retinol (sphingosome: a kind of multi lamellar liposome) is produced.

The above sphingosome has a form of a multi-lamellar liposome and has a mean diameter of less than 300 nm. The detailed composition of the sphingosome comprises: lecithin in an amount of 1.0~15.0 weight %, ceramide in an amount of 0.1~10.0 weight %, oily carrier in an amount of 5.0~40.0 weight %, nonionic surface-active agent vesicle in an amount of 10.0~60.0 weight %, polyhydric alcohol in an amount of 2.0~20.0 weight %, alcohol solution in an amount of 20.0~50.0 weight % with respect to the entire sphingosome composition. Retinol is stabilized secondly by addition into this sphingosome.

The lecithin used is a saturated form obtained by mixing it with water, and can be selected from among soybean, egg yolks or plant seeds. Ceramide is selected from synthetic sphingosine, fermented sphingosine, natural sphingosine from fungi, animal and plant, their derivatives and cerebroside. In this invention, oily carrier is a common name of most oily material, which is in liquid state at room temperature, and can be selected from among vegetable oil, animal oil, synthetic oil, mineral oil, silicone oil, and silicone derivatives. Polyhydric alcohol can be selected from among glycerine, propylene glycol, dipropylene glycol, butylene glycol, isopropylene glycol, pentylene glycol and so on.

Stabilization Method III:

The above sphingosome prepared in stabilization method II is added to an O/W type emulsifying base having a lamellar liquid-crystal structure, which O/W type emulsifying base is produced by the uniform emulsification of a fat-phase with a water-phase. The fat-phase used in making the emulsifying base contains nonionic, anionic surface-active agent, higher fatty alcohol, higher fatty acid, ceramide, cholesterol, and phytosterol.

The emulsifying base has a lamellar liquid crystal structure, which is O/W type, and its detail composition comprises: nonionic, anionic surface-active agent in an amount of 0.1~20.0 weight %, higher fatty alcohol in an amount of 0.1~10.0 weight %, higher fatty acid in an amount of 0.1~10.0 weight %, ceramide 0.1~10.0 in an amount of weight %, cholesterol and its derivatives, phytosterol and its derivative in an amount of 0.1~10.0 weight % with respect to the entire base composition.

In this invention, nonionic or anionic surface-active agents are used chiefly among surface-active agents. The surface-active agent can be selected from among ethoxylated surface-active agent such as polyoxyethylene alkyl ether, polyoxyethylene paraffin and polyoxyethylene cholesteryl ester. Also, useful as a surface-active agent is EO(ethyleneoxide) free surface-active agent such as polyglyceryl alkylate, polyglyceryl alkyl glucose alkylate, alkyl glucoside, sorbitan alkylate, or sugar ester. The anionic surface-active agent is selected from among sodium alkyloyl lactylate, alkyl phosphate, polyalkyl ether phosphate. The higher fatty alcohol is selected from among natural alcohol where the total number of carbon atoms in the alcohol is from 10 to 30. The higher fatty acid is selected from among natural fatty acid where the total number of carbon atoms in the acid is from 8 to 30. Ceramide is selected from among synthetic sphingosine, fermented sphingosine, natural sphingosine from fungi, animals and plants. Derivatives of the forgoing sphingosines and cerebrosides also can be target material. Cholesterol and its derivatives can be selected from among cholesteryl alkylate and cholesteryl sulfate obtained by esterification of fatty acid and natural or synthetic cholesterol. Phytosterol and its derivatives can be selected from among beta-sitosterol, beta-sitosterol sulfate and so on.

As stated above, nonionic surface-active agent vesicles, which contain unstable fat-soluble active retinol, are added into multi lamellar liposomes consisting of phospholipid and ceramide. Thereby, doubly stabilized retinol (sphingosome) is made. Finally, the sphingosomes are added to an O/W type emulsifying base, so the retinol is triply stabilized.

This process is described in more detail as follows.

Unstable and fat-soluble active material, retinol to be stabilized, nonionic surface-active agent, cholesterol, phytosterol and oily carrier are mixed uniformly. Then fat-soluble active material and polyhydric alcohol aqueous solution are also added into the forgoing mixture. The total mixture is emulsified with high pressure, forming microvesicles, wherein retinol is contained in the core space of the vesicles. The vesicle has a mean diameter from 10 to 50 nanometres.

That is, unstable fat-soluble active material is inserted into the vesicles, so being firstly stabilized. Then lecithin and ceramide are melted with oily carrier. The aqueous phase composition is also added into the fat-phase and emulsified with high pressure. The emulsified mixture is emulsified again with first-stabilized nonionic surface-active agent vesicle, producing multilayered sphingosomes (a kind of multi lamellar liposome), of width less than 300 nm, enclosing vesicles located therein. Triple stabilized cosmetic material can be obtained by sphingosome being added into and mixed with an O/W type emulsifying base of lamellar liquid-crystal structure. And the emulsifying base is made by uniform emulsification of the aqueous phase and fat-phase. The fat-phase consists of nonionic, anionic surface-active agent, higher fatty alcohol, higher fatty acid, ceramide, cholesterol, and phytosterol.

The amount of retinol in the total compositions, according to the present invention, may range from 0.001 to 2.0%, preferably from 0.005 to 1.0% by weight. The amount of nonionic surface-active agent vesicle in the total compositions according to the present invention may range from 0.01 to 20.0%, preferably from 0.05 to 10.0% by weight. The amount of doubly stabilized retinol (sphingosome) in total compositions according to the present invention may range from 0.02 to 40.0%, preferably from 0.1 to 20.0% by weight.

Cosmetic compositions of the present invention may be in any form. The forms may include normally skin softner, nutrifying skin lotion, nutrifying creams, massage creams, essence, serum or compack.

The following examples will more fully illustrate embodiments of this invention

PREFERRED EMBODIMENT OF THE INVENTION

EXAMPLE 1

Production of Nonionic Surface-active Agent Vesicle

TABLE 1

Composition of nonionic surface-active agent vesicle.

unit: weight %

|   |   | Example 1-1 | Example 1-2 | Example 1-3 |
|---|---|---|---|---|
| A | Cholesterol | 3.00 | 8.00 | 8.00 |
|   | phytosterol | 5.00 | 5.00 | 5.00 |
|   | choleth-24 | 3.50 | 5.00 | 2.00 |
|   | ceteth-24 | — | — | 2.00 |
|   | steareth-4 | 1.50 | 3.00 | 2.00 |
|   | dicetylphosphate | 1.00 | 5.00 | 3.00 |
|   | capryliccaprictriglyceride | 10.00 | 18.00 | 18.00 |
| B | purified water | To 100 | To 100 | To 100 |
|   | glycerine | 5.00 | 5.00 | 5.00 |
| C | retinol 50% (in polysorbate 20) | 10.00 | 20.00 | 15.00 |
| Total |   | 100 | 100 | 100 |

Synthesis Procedure

The chemicals of A-phase are all mixed and heated to 70~80° C.
The A-phase mixture must be perfectly homogeneous.
The chemicals of B-phase are all mixed and heated to 70~80° C.
Then B-phase mixture is added into A-phase mixture.
The A,B-phase mixture is then stirred.
After the mixture is cooled sufficiently, Chemicals of C-phase are added into the A,B-phase mixture at low temperature.
The total mixed compound is passed through a high-pressure emulsifier.
Finally vesicles, which have a mean diameter of 10–50 nm, are made.

EXAMPLE 2

Production of Sphingosomes

TABLE 2

Composition of sphingosomes unit: weight %

|   |   | Example 2-1 | Example 2-2 | Example 2-3 |
|---|---|---|---|---|
| A | hydrogenated lecithin | 3.00 | 6.00 | — |
|   | lecithin | — | — | 8.00 |
|   | ceramide (03) | 0.50 | 0.70 | 0.50 |
|   | capryliccapricglyceride | 7.00 | 10.00 | 10.00 |
| B | propyleneglycol | 10.00 | 15.00 | 10.00 |
|   | ethanol | 5.00 | 10.00 | 10.00 |
|   | purified water | To 100 | To 100 | To 100 |
| C | nonionic surface-active agent vesticle (Example 1-2) | 30.00 | 50.00 | 40.00 |
| D | macadamia nut oil | 20.00 | 30.00 | 20.00 |
|   | jojoba oil | — | — | 10.00 |
| Total |   | 100.00 | 100.00 | 100.00 |

Synthesis Procedure

The chemicals of A-phase are all mixed, heated to 80–90° C. and melted.
Chemicals of B-phase are added into the A-phase mixture.
The A,B-phase mixture is passed through a high pressure emulsifier.
Chemicals of C-phase are added into the A,B-phase mixture and the A,B,C-phase mixture is passed through a high pressure emulsifier.
Chemicals of D-phase are all added into the former mixture.
The total mixture is stirred and passed through a high pressure emulsifier.
Thereby, sphingosomes are produced.

EXAMPLE 3

Production of Emulsifying Base

TABLE 3

Composition of emulsifying base unit: weight %

|   |   | Example 3-1 | Example 3-2 | Example 3-3 |
|---|---|---|---|---|
| A | Paraffin | 1.5 | 1.5 | 1.5 |
|   | glyceryl stearate | 2.5 | 2.5 | 2.5 |
|   | stearyl alcohol | 2.5 | 2.5 | 2.5 |
|   | stearic acid | 1.0 | 1.0 | 1.0 |
|   | trioctanoin | 5.0 | 5.0 | 5.0 |
|   | squalene | 5.0 | 5.0 | 5.0 |
|   | liquid paraffin | 3.0 | 3.0 | 3.0 |
|   | stearyl glucoside | 2.5 | — | 1.5 |
|   | polyglyceryl-3-methylglucose distearate | — | 2.5 | 1.5 |
|   | cholesterol | 0.5 | 0.5 | 0.5 |
|   | ceramide | 0.5 | 0.5 | 0.5 |
|   | tocopheryl acetate | 0.5 | 0.5 | 0.5 |
|   | BHT | 0.1 | 0.1 | 0.1 |
|   | Cyclomethicone | 1.0 | 1.0 | 1.0 |
| B | purified water | To 100 | To 100 | To 100 |
|   | glycerine | 5.0 | 5.0 | 5.0 |
|   | sorbitol | 2.0 | 2.0 | 2.0 |
|   | xanthan gum | 0.05 | 0.1 | 0.1 |
|   | triethanol amine | 0.5 | 0.5 | 0.5 |
|   | aroma, antiseptic | proper quantity | proper quantity | proper quantity |
| C | sphingosome (Example 2-2) | 2.0 | 2.0 | 2.0 |
| Total |   | 100 | 100 | 100 |

Synthesis Procedure
Chemicals of A-phase and Chemicals of B-phase are mixed, heated and melted to 75° C.
A-phase mixture is added into B-phase mixture.
The A,B-phase mixture is cooled to 40° C.
Chemicals of C-phase are added into the A,B-phase mixture and the total mixture is cooled to room temperature.

Example and Comparative Examples

Table 4 represents the compositions of the example and comparative examples in present invention. Chemicals of A-phase and B-phase are mixed, heated to 75° C., emulsified with high pressure and cooled to 40° C. Chemicals of C,D-phase are added and mixed with each other to produce the final product.

Comparative example 1: A product wherein retinol is added into a normal cream base (a product that is not stabilized in triplicate)

Comparative example 2: A product wherein nonionic surface-active agent is added into a normal cream base (a product that is singly stabilized)

Comparative example 3: A product wherein sphingosomes are added into a normal cream base (a product that is doubly stabilized)

2. Experimental Method

The titer of retinal in all examples is measured directly after production.

Then, the temperatures of all examples are maintained at about 45 □ during one month.

TABLE 4

|   |   | unit: weight % | | | |
|---|---|---|---|---|---|
|   |   | Example 1 | C. example1 | C. example2 | C. example3 |
| A | paraffin | 1.5 | 1.5 | 1.5 | 1.5 |
|   | glyceryl stearate | 2.5 | 3.0 | 3.0 | 3.0 |
|   | stearyl alcohol | 2.5 | 1.2 | 1.2 | 1.2 |
|   | stearic acid | 1.0 | 0.5 | 0.5 | 0.5 |
|   | trioctanoin | 5.0 | 5.0 | 5.0 | 5.0 |
|   | squalene | 5.0 | 5.0 | 5.0 | 5.0 |
|   | liquid paraffin | 3.0 | 3.0 | 3.0 | 3.0 |
|   | stearyl glucoside | 2.5 | — | — | — |
|   | cholesterol | 0.5 | — | — | — |
|   | ceramide | 0.5 | — | — | — |
|   | tocopheryl acetate | 0.5 | 0.5 | 0.5 | 0.5 |
|   | BHT | 0.1 | 0.1 | 0.1 | 0.1 |
|   | cyclomethicone | 1.0 | 1.0 | 1.0 | 1.0 |
|   | sorbitan stearate | — | 0.5 | 0.5 | 0.5 |
|   | polysorbate 60 | — | 2.0 | 2.0 | 2.0 |
| B | purified water | To 100 | To 100 | To 100 | To 100 |
|   | glycerine | 5.0 | 5.0 | 5.0 | 5.0 |
|   | sorbitol | 2.0 | 2.0 | 2.0 | 2.0 |
|   | Xanthan gum | 0.05 | 0.1 | 0.1 | 0.1 |
|   | triethanol amine | 0.5 | 0.5 | 0.5 | 0.5 |
|   | aroma, antiseptic | proper quantity | proper quantity | proper quantity | proper quantity |
| C | nonionic vesicle (Ex 1-2) | — | — | 1.0 | — |
|   | sphingosome (Ex 2-2) | 2.0 | — | — | 2.0 |
| D | retinol solution 10% (in soybean oil) | — | 1.0 | — | — |
| Total |   | 100 | 100 | 100 | 100 |

Experiment 1: Titer Test

1. Products Used in Experiment

Example 1: A product wherein sphingosome is added into a lamella liquid crystal-forming cream base (triply stabilized product—present invention)

After one month the titer is measured again.

The measured titers of the examples are compared by reading the absorbance at 325 nm in HPLC.

The measured values are shown in table 5

TABLE 5

|   | C. Ex.1 | | C. Ex.2 | | C. Ex.3 | | Ex.1 | |
|---|---|---|---|---|---|---|---|---|
|   | Day 1 | Day 30 | Day 1 | Day 30 | Day 1 | Day 30 | Day 1 | Day 30 |
| Retinol titer value (%) | 98.9% | 30.5% | 98.6% | 71.5% | 98.2% | 81.7% | 98.7% | 92.5% |

From table 5, it is evident that the titer of comparative example 1 is lowered considerably. The titer of comparative examples 2 and 3 showed that the retinal of those examples was well-preserved.

The titer of example 1, conserved very well, in particular showed that the retinal of this example was retaining at over 92.0% even at high temperature. Thus, unstable retinal is stabilized well in the composition of example 1.

Experiment 2: Skin Irritation Test 1. products used in the experiment: identical with example 1
2. Experimental method: The degree of skin irritation is measured by closed-patch-method. In this method, after the patch is attached for 24 hours, the degree of irritation is measured and evaluated. The relative value compared of irritation is measured. The value is 0 in case of no skin irritation, 5 in case of serious irritation.

The measured values are shown in table 6

TABLE 6

| Example | degree of skin irritation |
| --- | --- |
| Comparative example 1 | 4.00 |
| Comparative example 2 | 2.50 |
| Comparative example 3 | 1.50 |
| Example 1 | 0.90 |

From table 6, it is evident that retinol, which is doubly stabilized within the sphingosome and lamellar liquid crystal, is released to the skin very slowly. Thus, the present invention prevents skin from contact with excessive retinol and so skin irritation is minimized.

Experiment 3: Discoloration Test

1. Products used in experiment: identical with example 1
2. Experimental method: The discoloration of products was evaluated with colormeter over two weeks at 4° C. and 45° C. In this method the relative color change is measured. Standard value is 0 in case of no color change, 5 in case of serious color change.

TABLE 7

| Product | Temp. | Degree of color change |
| --- | --- | --- |
| Comparative example 1 | 45° | 5.0 |
|  | 4° | 1.2 |
| Comparative example 2 | 45° | 2.5 |
|  | 4° | 0.5 |
| Comparative example 3 | 45° | 1.3 |
|  | 4° | 0 |
| Example 1 | 45° | 0.6 |
|  | 4° | 0 |

Retinol is very sensitive to temperature, and its thermal degradation results in serious discoloration at high temperature. But from table 7, it is evident that the present invention is very stable even at high temperature, so titer and color can be preserved.

Experiment 4: Test for Skin Elasticity

1. Products used in experiment: identical with example 1
2. Experimental method: Twenty healthy women, whose skin surface temperature is maintained evenly within the range of 24~26° C., and whose skin humidity is maintained evenly within the range of 38~40%, were selected. Two products were spreaded on the both sides of the face and the elasticity of the skin was measured with Cutometer SEM 74 for over 3 months. Standard value is 0 in case of no elasticity, 5 in case of good elasticity.

The measured values are in table 8

TABLE 8

| Product | Degree of elasticity |
| --- | --- |
| Comparative example 1 | 1.3 |
| Comparative example 2 | 3.2 |
| Comparative example 3 | 4.0 |
| Example 1 | 4.4 |

From table 8, it is evident that the encapsulated retinol of the present invention is superior in moisturizing effect because it forms a lamella liquid crystal structure similar to the lipid-texture of the skin. And the product having doubly stabilized sphingosomes, consisting of phospholipids, and having a width of less than 300 nm, enables retinol to penetrate the skin easily. So, it promotes protein biosynthesis and improves the moisturizing effect and elasticity of skin.

If unstable useful fat-soluble active retinol is stabilized with present invention, retinol is released to the skin very slowly because of its encapsulation within sphingosome and lamellar liquid crystal structure. So cosmetic materials which cause little skin irritation regardless of excessive treatment, can be realized.

Therefore this invention can provide a lasting treatment effective for wrinkling, acne, elasticity improvement, skin tone improvement, moisturizing, and recovery from skin injury.

What is claimed is:

1. A cosmetic composition, comprising triple-stabilized retinol, said retinol being firstly encapsulated with vesicles comprising 4.0~20.0 weight % of a nonionic surface-active agent, 0.1~10.0 wt % of an alkyl phosphate, 0.1~20.0 wt % of retinol, 5.0~30.0 wt % of an oily carrier, 1.0~20.0 wt % of cholesterol derivatives, and 20.0~55.0 wt % of a polyhydric alcohol aqueous solution, based on the total weight of the cosmetic composition, secondly with sphingosomes comprising 1.0~15.0 wt % of lecithin, 0.1~10.0 wt % of ceramide, 5.0~40.0 wt % of an oily carrier, 10.0~60.0 wt % of the vesicles, 2.0~20.0 wt % of polyhydric alcohol, and 20.0~50.0 wt % of an alcohol solution, based on the total weight of the cosmetic composition, and thirdly with an O/W lamellar emulsifying base comprising 0.1~20.0 wt % of an anionic surface-active agent, 0.1~10.0 wt % of a higher fatty alcohol, 0.1~10.0 wt % of a higher fatty acid, and 0.1~10.0 wt % of ceramide, based on the total weight of the cosmetic composition.

2. The cosmetic composition according to claim 1, comprising the retinol in the amount of 0.001~2.0 weight %, the vesicles in the amount of 0.01~20.0 weight %, and the sphingosomes in the amount of 0.02~40.0 weight % based on the total weight of the composition.

3. The cosmetic composition according to claim 1, wherein the vesicles are monolayer with a mean diameter of 10~50 nanometers.

4. The cosmetic composition according to claim 1, wherein the alkyl phosphate is selected from the group consisting of monoalkyl phosphate, dialkyl phosphate, trialkyl phosphate and polyoxyethylene alkylphosphate.

5. The cosmetic composition according to claim 1, wherein the oily carrier is selected from the group consisting of vegetable oil, animal oil, synthetic oil, mineral oil, silicone oil, and silicone derivatives.

6. The cosmetic composition according to claim 1, wherein the polyhydric alcohol is selected from the group consisting of glycerine, propyleneglycol, dipropyleneglycol, butyleneglycol, isopropyleneglycol and pentyleneglycol.

7. The cosmetic composition according to claim 1, wherein the cholesterol derivative is produced by the esterification of cholesterol and fatty acid and selected from the group consisting of cholesteryl stearate, cholesteryl isostearate, cholesteryl alkylate and cholesteryl sulfate.

8. The cosmetic composition according to claim 1, wherein the phylosterol derivative is selected from the group consisting of beta-sitosterol, and beta-sitosterol sulfate.

9. The cosmetic composition according to claim 1, wherein the nonionic surface-active agent is selected from the group consisting of polyglyceryl alkylate, polyglyceryl alkylglucose alkylate, alkylglucoside, sorbitan alkylate, sugar ester and an ethoxylated surface-active agent selected from among polyoxyethylene alkylether, polyoxyethylene paraffin, and polyoxyethylene cholesteryl ether.

10. The cosmetic composition according to claim 1, wherein the anionic surface-active agent is selected from the group consisting of sodium alkyloyl lactylate, alkylphosphate, and polyalkyl ether phosphate sugar ester.

11. The cosmetic composition according to claim 1, wherein the lamellar emulsifying base comprises a nonionic surface-active agent in the amount of 0.1~20.0 weight %, a higher fatty alcohol in the amount of 0.1~10.0 weight %, a higher fatty acid in the amount of 0.1~10.0 weight %, ceramide 0.1~10.0 in the amount of weight % based on the total weight of the cosmetic composition.

12. The cosmetic composition according to claim 1, wherein the higher fatty alcohol contains 10 to 30 carbon atoms.

13. The cosmetic composition according to claim 1, wherein the higher fatty acid contains 8 to 30 carbon atoms.

14. The cosmetic composition according to claim 1, wherein the vesicles comprise a nonionic surface-active agent in the amount of 4.0~20.0 weight %, alkyl phosphate in the amount of 0.1~10.0 weight %, a fat-soluble active material in the amount of 0.1~20.0 weight %, an oily carrier in the amount of 5.0~30.0 weight %, phytosterol and its derivatives in the amount of 1.0~20.0 weight %, and a polyhydric alcohol aqueous solution in the amount of 20.0~55.0 weight %.

15. The cosmetic composition according to claim 1, wherein the oily carrier is selected from the group consisting of vegetable oil, animal oil, synthetic oil, mineral oil, silicone oil, and silicone derivatives.

16. The cosmetic composition according to claim 1, wherein the polyhydric alcohol is selected from the group consisting of glycerine, propyleneglycol, dipropyleneglycol, butyleneglycol, isopropyleneglycol and pentyleneglycol.

* * * * *